US012588932B2

(12) United States Patent
Cundiff et al.

(10) Patent No.: US 12,588,932 B2
(45) Date of Patent: Mar. 31, 2026

(54) MULTI-PLANAR FIXATION SYSTEM

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Scott Maling, Scottsdale, AZ (US); Mark William Roberts, Jr., Gilbert, AZ (US); Eli W. Jacobson, Chandler, AZ (US)

( * ) Notice: Subject to any disclaimer, the term of this patent is extended or adjusted under 35 U.S.C. 154(b) by 539 days.

(21) Appl. No.: 18/104,262

(22) Filed: Jan. 31, 2023

(65) Prior Publication Data

US 2024/0252210 A1     Aug. 1, 2024

(51) Int. Cl.
    *A61B 17/68*     (2006.01)
    *A61B 17/17*     (2006.01)
    *A61B 17/56*     (2006.01)

(52) U.S. Cl.
    CPC .......... *A61B 17/68* (2013.01); *A61B 17/1775* (2016.11); *A61B 2017/564* (2013.01)

(58) Field of Classification Search
    CPC ................ A61B 17/68; A61B 17/1775; A61B 2017/564
    See application file for complete search history.

(56) References Cited

U.S. PATENT DOCUMENTS 9,545,276 B2      1/2017 Buchanan
2014/0277176 A1*  9/2014 Buchanan .......... A61B 17/8057
                                                    606/280

OTHER PUBLICATIONS

Arthrex, Plantar Lapidus Plate Surgical Technique, 2019, https://www.arthrex.com/foot-ankle/lapidus-plate.

* cited by examiner

*Primary Examiner* — Sameh R Boles

(57)     ABSTRACT

Osteotomy fixation systems and surgical methods are provided herein. A fixation system can comprise a body, a curved portion, a dorsal extension, a medial extension, and at least three fixation holes. The curved portion can be configured to conform to a curvature of a first cuneiform. The dorsal extension can be configured to conform to a curvature of a dorsal side of a first metatarsal. The medial extension can be configured to conform to a curvature of a medial side of the first metatarsal.

16 Claims, 8 Drawing Sheets

MULTI-PLANAR FIXATION SYSTEM

FIELD OF THE TECHNOLOGY

The present technology relates generally to surgical instruments and techniques, and more particularly to, osteotomy fixation systems and surgical techniques.

BACKGROUND

Different surgical procedures utilize different instruments and techniques. In an osteotomy for correcting a bunion, for example, the surgeon compresses the first cuneiform and first metatarsal to promote fusion. This compression can be assisted by utilizing a fixation plate Sometimes the joint between the first cuneiform and the first metatarsal requires multiple fixation plates to stabilize the joint. Multiple fixation plates typically require a longer surgical procedure and can be difficult to align properly.

SUMMARY

A device comprising a body and at least one fixation device. The body can comprise a curved portion, a dorsal extension, a medial extension, and at least three fixation holes. The fixation holes can each be configured to receive the respective fixation device. Each of the fixation holes can extend through the body. At least one fixation hole can be on the curved portion. At least one fixation hole can be on the dorsal extension. At least one fixation hole can be on the medial extension. The fixation hole(s) on the dorsal extension and on the medial extension can be offset with respect to one another. Each fixation hole can be threaded, un-threaded, locking, non-locking, and/or scalloped. The fixation device can be a screw, a locking screw, a k-wire, an olive pin, a suture, and/or a nail.

Each fixation hole can define a respective insertion area and each fixation hole can be configured to allow its respective fixation device to be inserted therein. At least one insertion area can comprise a conical shape. The conical shape can comprise an angle between 25 degrees and 35 degrees.

The curved portion can be configured to conform to a first curvature of the medial cuneiform. The dorsal extension can be configured to conform to a dorsal curvature of the first metatarsal. The medial extension can be configured to conform to a medial curvature of the first metatarsal. The dorsal curvature and the medial curvature can be the same curvature, or they can be different curvatures. The body can be configured to at least partially surround a metatarsal flare. The body can compress, or hold the compression of a metatarsal to a cuneiform.

A distal end of the dorsal extension can define a first angle. A distal end of the medial extension can define a second angle. The first angle and the second angle can intersect at a third angle. The third angle can be between 80 degrees and 100 degrees.

The curved portion can comprise a dorsal portion and a medial portion. The dorsal portion can define a fourth angle. The medial portion can define a fifth angle. The fourth and fifth angle can intersect to form a sixth angle. The sixth angle can be between 30 degrees and 60 degrees.

A surgical method includes aligning a curved portion of a body with the medial cuneiform of a subject. Aligning a dorsal extension of the body with the dorsal side of the first metatarsal of the subject. Aligning a medial extension of the body with the medial side of the first metatarsal. Inserting a first fixation device through a first fixation hole on the dorsal extension and into the dorsal side of the first metatarsal. Inserting a second fixation device through a second fixation hole on the medial extension and into the medial side of the first metatarsal. Inserting a third fixation device through a third fixation hole on the curved portion and into the medial cuneiform. Aligning the first metatarsal and the medial cuneiform in a plurality of planes and preparing the first metatarsal and the medial cuneiform for fusion. Aligning the first metatarsal with the medial cuneiform in the plurality of planes can be done before or after preparing the first metatarsal and/or medial cuneiform for fusion.

The method can further comprise the second fixation device comprising a first longitudinal axis, and the third fixation device comprising a second longitudinal axis. The first longitudinal axis and the second longitudinal axis can form an angle that is in the range of 80 degrees to 100 degrees.

Inserting the first fixation device into the medial cuneiform can further comprise inserting the first fixation device into the first cuneiform and into a second cuneiform.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

It should be understood that the language used in the present disclosure has been principally selected for read-ability and instructional purposes, and not to limit the scope of the subject matter disclosed herein in any manner. Fur-ther, reference throughout this specification to "one embodi-ment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and varia-tions thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Furthermore, the described features, structures, or characteristics of the various embodiments disclosed herein may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Various embodiments provide osteotomy fixation systems and surgical techniques. Some osteotomy fixation systems include a body and a fixation device. Various surgical techniques perform an osteotomy using one embodiment of an osteotomy fixation system.

Figure 1:
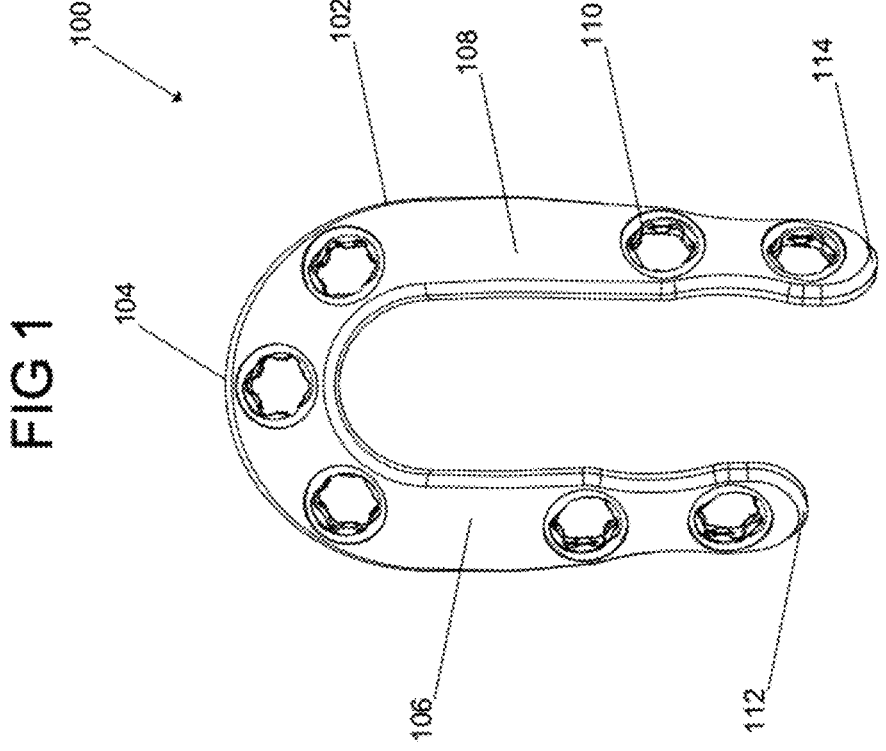
FIG. 1 is a diagram illustrating one embodiment of a fixation system.
Figure 2:
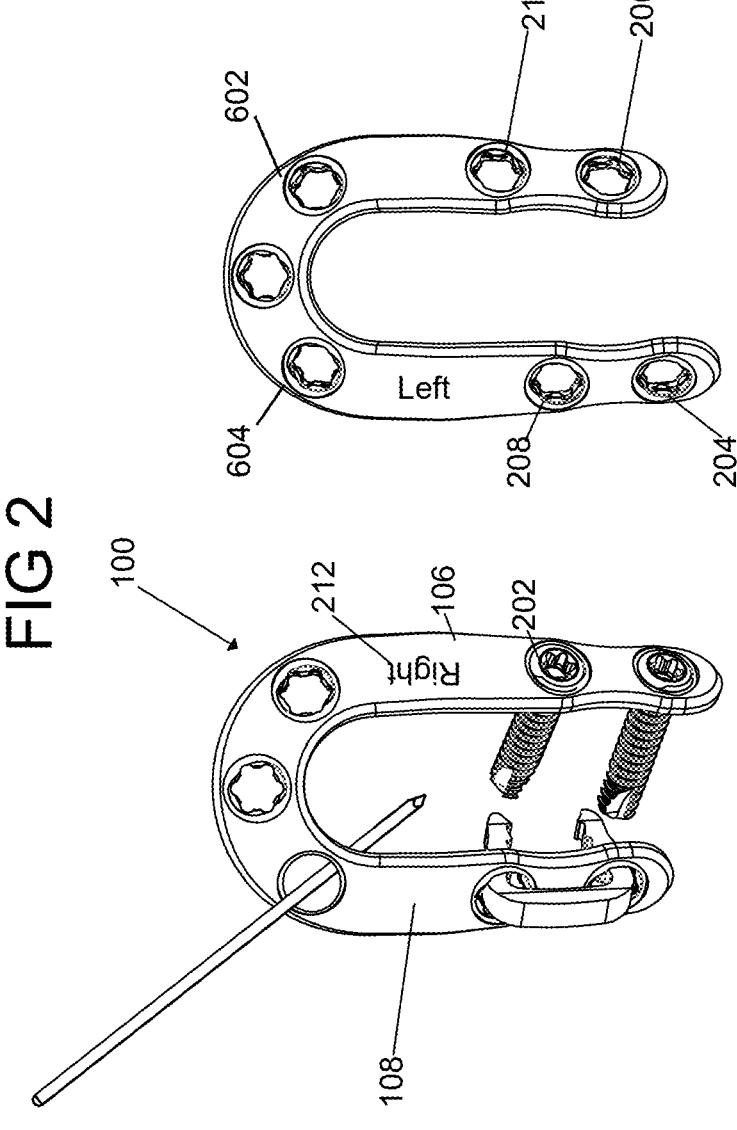
FIG. 2 is a diagram illustrating one embodiment of a fixation system.

Turning now to the drawings, FIGS. 1 and 2 are diagrams illustrating one embodiment of a fixation system 100. At least in the illustrated embodiment, the fixation system 100 includes, among other components, a body 102 that can comprise a curved portion 104, a dorsal extension 106 and a medial extension 108. The body 102 further comprises a plurality of fixation holes 110.

In at least one embodiment the curved portion 104, the dorsal extension 106, and the medial extension 108 can each comprise at least one fixation hole 110. In some embodiments the curved portion 104, the dorsal extension 106, and/or the medial extension 108 can have more or less than one fixation hole 110, respectively.

In at least one embodiment the body 102 can be comprised of two or more pieces that can be coupled to form the body 102. Additionally, the curved portion 104, the dorsal extension 106, and the medial extension 108 can be integral or separate.

Each fixation hole 110, in various embodiments, can be threaded, non-threaded, locking, non-locking, and/or scalloped. The fixation hole 110 can be circular or oblong, along with other shapes that are possible and contemplated herein. In certain embodiments, the fixation hole(s) 110 can be configured to receive a fixation device 202.

A fixation device 202 can include any suitable device, system, and/or structure that is capable of at least temporarily fixing, attaching, coupling, connecting, and/or mating the body 102 to another object, such as, for example, a bone, among other suitable objects, each of which is contemplated herein. The fixation device 202 can include, for example, a screw, a locking screw, a wire, a pin, a suture, and/or a nail, among other devices that are possible and contemplated herein.

The body 102, in various embodiments, may be formed of any suitable material, such as, for example, titanium, titanium alloy, nickel, nickel alloy, nickel titanium alloy, stainless steel, and the like, as well as plastics, radio-translucent materials and/or other materials that are possible, each of which and combinations of such are each contemplated herein. In certain embodiments, the material included in and/or forming the body 102 is sterilizable.

At least in the embodiments illustrated in FIGS. 1 and 2, the dorsal extension 106 and the medial extension 108 each comprise at least one fixation hole 110. The fixation hole(s) 110 on the dorsal extension 106 can be offset with respect to the fixation hole(s) 110 on the medial extension 108 so as to allow for insertion of the fixation device 202 in the dorsal extension 106 fixation hole(s) 110 without interfering with inserting the fixation device 202 in the medial extension 108 fixation hole(s) 110. In at least one embodiment the fixation hole(s) 110 on the medial extension 108 are more distal than the fixation hole(s) 110 on the dorsal extension 106. In at least one embodiment the fixation hole(s) 110 on the dorsal extension 106 are more distal than the fixation holes 110 on the medial extension 108. In at least one embodiment the dorsal extension 106 can comprise a plurality of fixation holes 110 and the medial extension 108 can comprise a plurality of fixation holes 110. The fixation holes 110 on the dorsal extension 106 can alternate with the fixation holes 110 on the medial extension 108. For example (FIG. 2), a first fixation hole 204 on the dorsal extension 106 can be more distal than a second fixation hole 206 on the medial extension 108 which can be more distal than a third fixation hole 208 on the dorsal extension 106 which can be more distal than a fourth fixation hole 210 on the medial extension 108. The dorsal extension 106 and the medial extension 108 can comprise more or fewer fixation holes that alternate in a like manner. In an additional or alternative embodiment, the fixation hole(s) 110 on the dorsal extension 106 can be aligned with the fixation hole(s) 110 on the medial extension 108.

In at least one embodiment, the dorsal extension 106 can comprise a dorsal distal end 112 including a fixation hole 110 at the dorsal distal end 112. In an additional or alternative embodiment, the medial extension 108 comprises a medial distal end 114 including a fixation hole 110 at the medial distal end 114.

Figure 3:
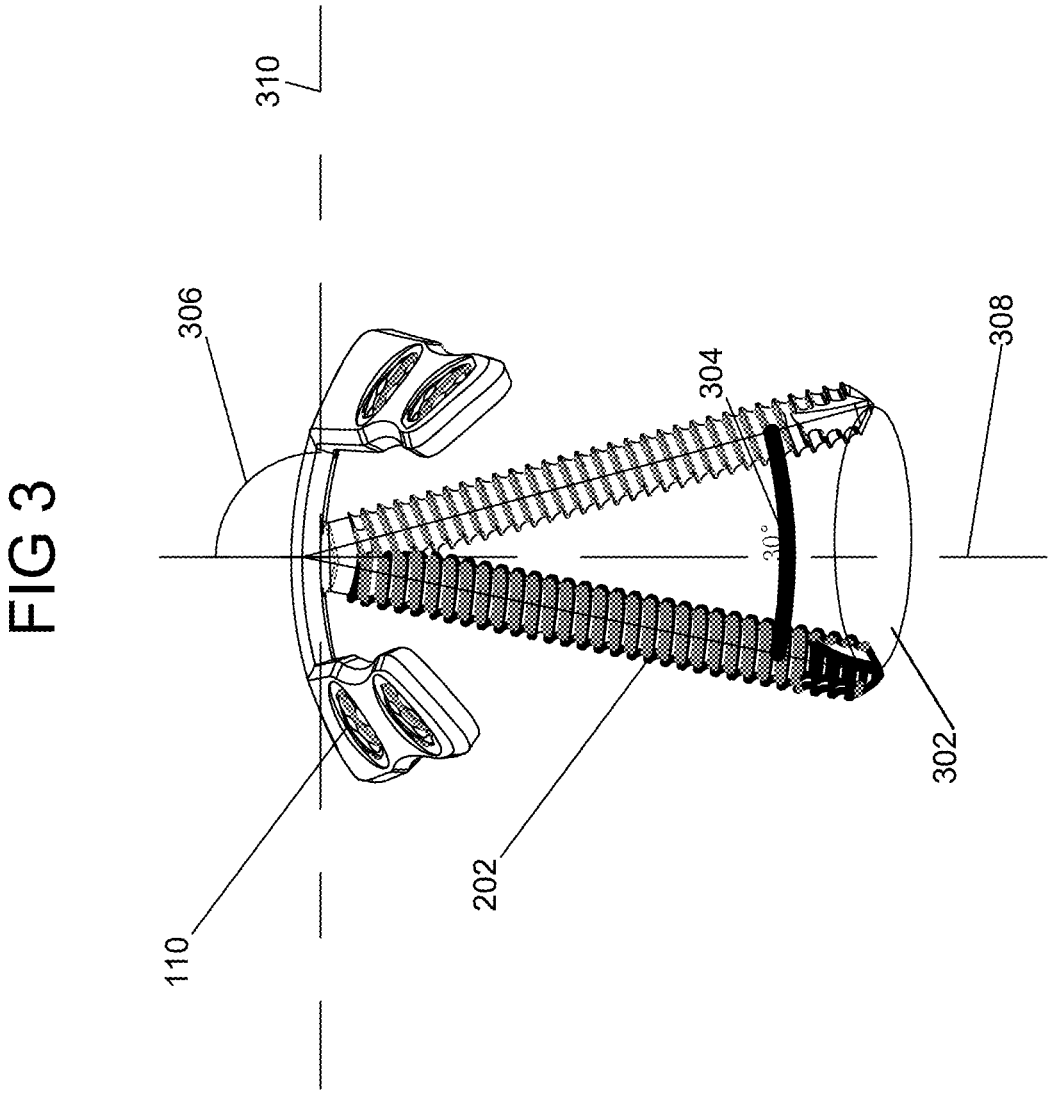
FIG. 3 is a diagram illustrating one embodiment of a fixation system.

At least in the embodiments illustrated in FIG. 3, each fixation hole 110 defines an insertion area 302. The insertion area 302 can include a volume wherein an inserted fixation device 202 can be placed therein. A fixation hole 110 can allow for the fixation device 202 to have some flexibility as to the angle at which it is inserted. In some embodiments, this flexibility can allow for the fixation device 202 to be inserted perpendicular/normal to (e.g., 90 degrees (90°)) or about 90 degrees with respect to the body 102. In some embodiments the fixation device 202 can be inserted within an insertion angle, which can be any angle in the range of about 75 degrees (75°) to about 105 degrees (105°), inclusive, among other suitable angles that are less than about 75° or greater than about 105° that are possible, each of which is contemplated herein. In at least one embodiment the insertion area 302 can be cone shaped or substantially conical in shape. In some embodiments the insertion area 302 can include a cone angle 304, which can be any angle in the range of about 20 degrees (20°) to about 40 degrees (40°), inclusive, among other suitable angles that are less than about 20° or greater than about 40° that are possible, each of which is contemplated herein.

Figure 4A:
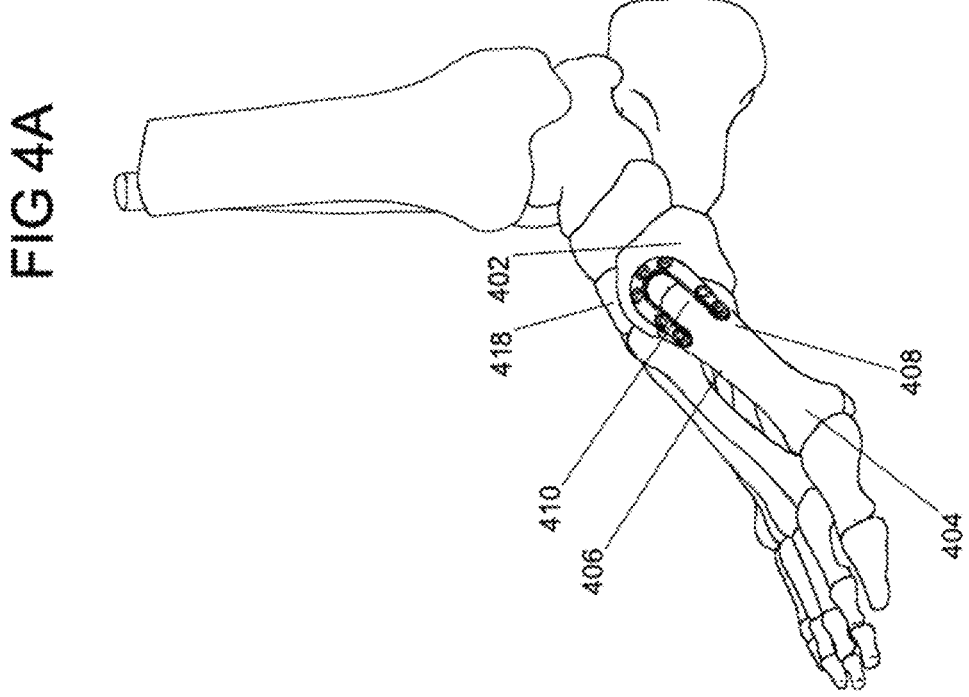
FIG. 4A is a diagram illustrating one embodiment of a fixation system on a foot.
Figure 4B:
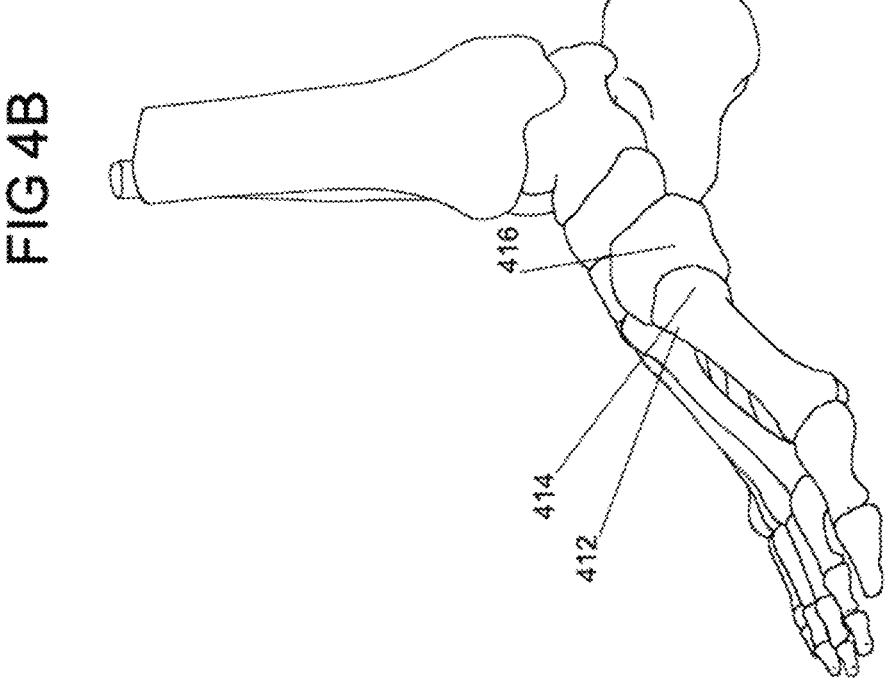
FIG. 4B is a diagram illustrating a foot.

At least in the embodiment illustrated in FIGS. 4A and 4B, the curved portion 104 can be configured to conform to a curvature 416 of a medial cuneiform 402 of a subject (e.g., a human, an animal, etc.). Similarly, the dorsal extension 106 can be configured to conform to a curvature and/or declination angle 412 of a dorsal side 406 of a first metatarsal 404 of a subject so as to allow for fixation in at least a first plane.

The medial extension 108, in at least some embodiments, can be configured to conform to a curvature and/or declination angle 414 of a medial side 408 of the first metatarsal 404 so as to allow for fixation in at least second plane. In some embodiments, the dorsal curvature 412 and the medial curvature 414 include the same curvature and/or angle, or substantially the same curvature and/or angle, in which case the same body 102 can be used on a left foot or a right foot of a subject.

In other embodiments, the dorsal curvature 412 and the medial curvature 414 include different curvatures and/or angles, optimizing the fixation system 100 for use on either the left foot or the right foot of a subject. The body 102, in certain embodiments, can comprise a label 212 (FIG. 2) indicating which foot (e.g., left, right, or left and right) or feet is/are the intended recipient for the fixation system 100. Other labels and/or types of labels is/are possible, each of which is contemplated herein.

In at least one embodiment, the body is configured to conform to a curvature 416 of the medial cuneiform 402 of a subject, the curvature 412 of the dorsal side 406 of the first metatarsal 404 of a subject, the curvature 414 of the medial side 408 of the first metatarsal 404 of a subject, and to at least partially surround a metatarsal flare 410 of a subject.

Figure 5:
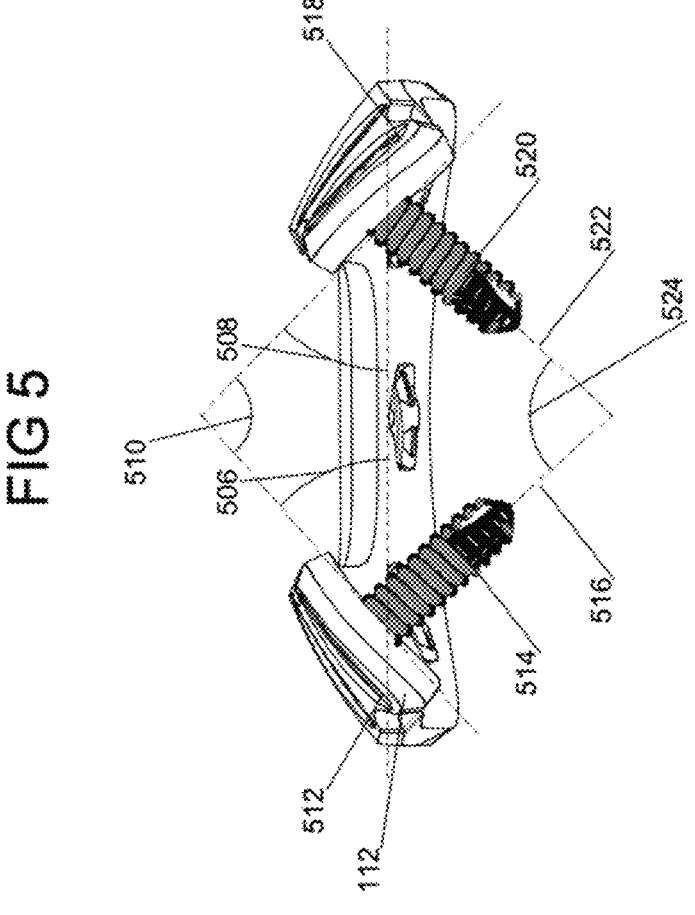
FIG. 5 is a diagram illustrating one embodiment of a fixation system.

At least in the embodiment illustrated in FIG. 5, the dorsal distal end 112 can be curved such that it can create a first angle 506. The medial distal end 114 can be curved such that it can create a second angle 508. The first angle 506 and the second angle 508 can intersect to create a third angle 510.

The third angle 510 can be any angle in the range of about 70 degrees (70°) to about 110 degrees (110°), inclusive, among other suitable angles that are less than about 70° or greater than about 110° that are possible, each of which is contemplated herein. The third angle 510 can enable fixation system 100 to be at least a bi-planar fixation system including fixation in a generally sagittal, generally transverse, and/or frontal plane(s). The first angle 506 and the second angle 508 can include the same angle and/or degree amount, or they can include different angles and/or degree amounts.

In one or more embodiments, the dorsal distal end 112 can comprise a first fixation hole 512 and a first fixation device 514 including a first longitudinal axis 516. In additional or alternative embodiments, the medial distal end 114 can comprise a second fixation hole 518 and a second fixation device 520 including a second longitudinal axis 522. In various embodiments, the first longitudinal axis 516 and the second longitudinal axis 522 can intersect in a frontal plane (e.g., a view from the front of the target toe of a subject) to create a first axis angle 524 that is generally orthogonal, or any angle in the range of about 80 degrees (80°) to about 100 degrees (100°), inclusive, among other suitable angles that are less than about 80° or greater than about 100° that are possible, each of which is contemplated herein.

Figure 6:
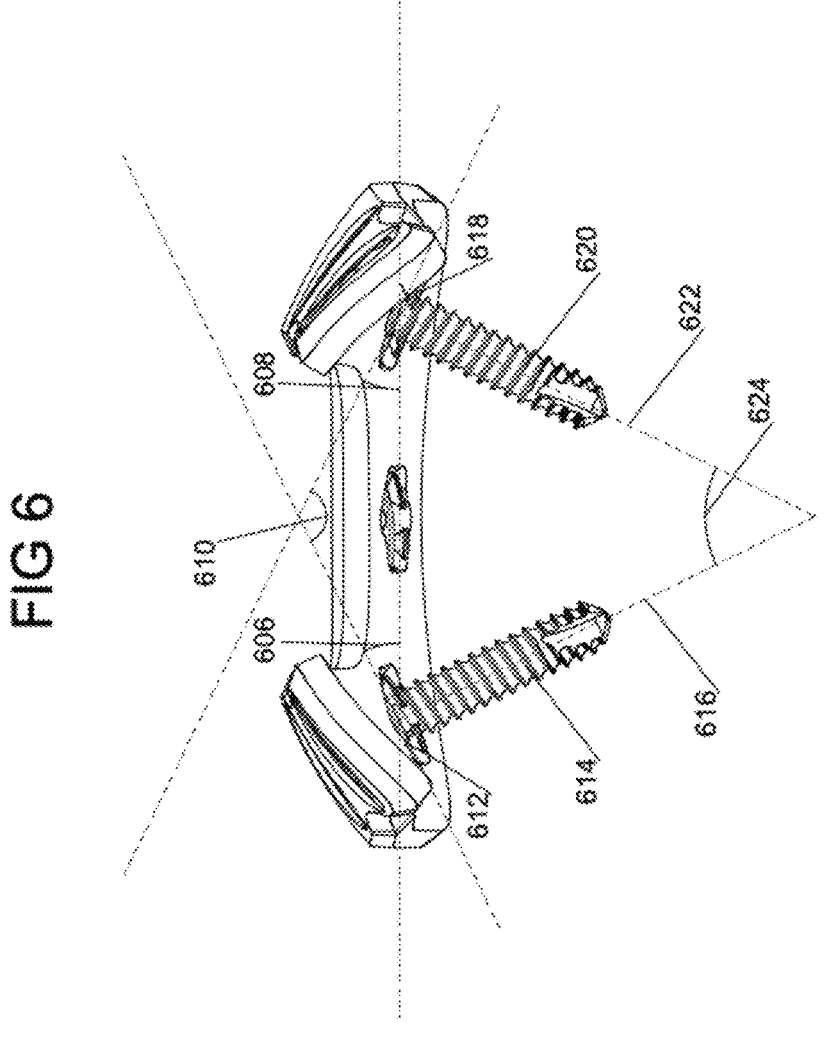
FIG. 6 is a diagram illustrating one embodiment of a fixation system.

At least in the embodiment illustrated in FIG. 6, the curved portion 104 can comprise a dorsal portion 602 and a medial portion 604. The dorsal portion 602 can be curved such that it can create a fourth angle 606. The medial portion 604 can be curved such that it can create a fifth angle 608.

The fourth angle 606 and the fifth angle 608 can intersect to create a sixth angle 610. The sixth angle can be any angle in the range of about 20 degrees (20°) to about 70 degrees (70°), inclusive, among other suitable angles that are less than about 20° or greater than about 70° that are possible, each of which is contemplated herein. In some embodiments the sixth angle 610 can be any angle in the range of about 30 degrees (30°) to about 60 degrees (60°), inclusive, among other suitable angles that are less than about 30° or greater than about 60° that are possible, each of which is contemplated herein.

The fourth angle 606 and the fifth angle 608, in some embodiments, can include the same angle or degree amount. In other embodiments, the fourth angle 606 and the fifth angle 608 can include different angles and/or degree amounts.

In one or more embodiments, the dorsal portion 602 can comprise a third fixation hole 612 and a third fixation device 614 including a third longitudinal axis 616. The medial portion 604 can comprise a fourth fixation hole 618 and a fourth fixation device 620 including a fourth longitudinal axis 622.

The third axis 616 and the fourth axis 622 can intersect in the frontal plane (e.g., a view from the front of the toe of a subject) such that they form a second axis angle 624. The second axis angle 624 can be any angle in the range of about 20 degrees (20°) to about 70 degrees (70°), inclusive, among other suitable angles that are less than about 20° or greater than about 70° that are possible, each of which is contemplated herein. In some embodiments, the second axis angle 624 can be any angle in the range of 30 degrees (30°) to about 60 degrees (60°), inclusive, among other suitable angles that are less than about 30° or greater than about 60° that are possible, each of which is contemplated herein.

In use in accordance with at least one embodiment, the fixation system 100 can be used to fix two portions of the same bone (e.g., a first cuneiform or a first metatarsal, etc.), or two different bones (e.g., a first cuneiform and a first metatarsal, etc.) for fusion by performing the steps of: (1) aligning the curved portion 104 with the first cuneiform 402 of a subject; (2) inserting the fixation device 202 into the at least one fixation hole 110 on the curved portion 104 and into the first cuneiform 402 of the subject; (3) aligning the dorsal extension 106 with the dorsal side 406 of the first metatarsal 404 of the subject; (4) inserting the fixation device 202 into the at least one fixation hole 110 on the dorsal extension 106 and into the dorsal side of the first metatarsal of the subject; (5) aligning the medial extension 108 with the medial side 408 of the first metatarsal 404; (6) inserting the fixation device 202 into the at least one fixation hole 110 on the medial extension 108 and into the medial side of the first metatarsal of the subject.

The above steps can be performed in any suitable order and do not need to be performed in the listed order. In other words, the various embodiments are not limited to the order discussed above. As one example, the curved portion 104 and the dorsal extension 106 can be aligned before the fixation device(s) 202 is/are inserted into the fixation hole(s) 110. As another example, the fixation device(s) 202 can be inserted into the first metatarsal 404 and/or first cuneiform 402 before the body 102 is aligned with the first cuneiform 402 and/or first metatarsal 404.

When being used in a bunion correction procedure, at least one portion of the body 102 can be aligned after the first metatarsal 404 and first cuneiform 402 are aligned, during alignment of the first metatarsal 404 and cuneiform 402, or before alignment of the first metatarsal 404 and first cuneiform 402. The procedure, in various embodiments, can further include compressing the first cuneiform 402 and the first metatarsal 404.

Each fixation device 202 can be a temporary fixation device 202 or a permanent fixation device 202. The fixation system 100, in various embodiments, can comprise all temporary fixation devices 202, all permanent fixation devices 202, or any combination of temporary and permanent fixation devices 202.

Figure 7:
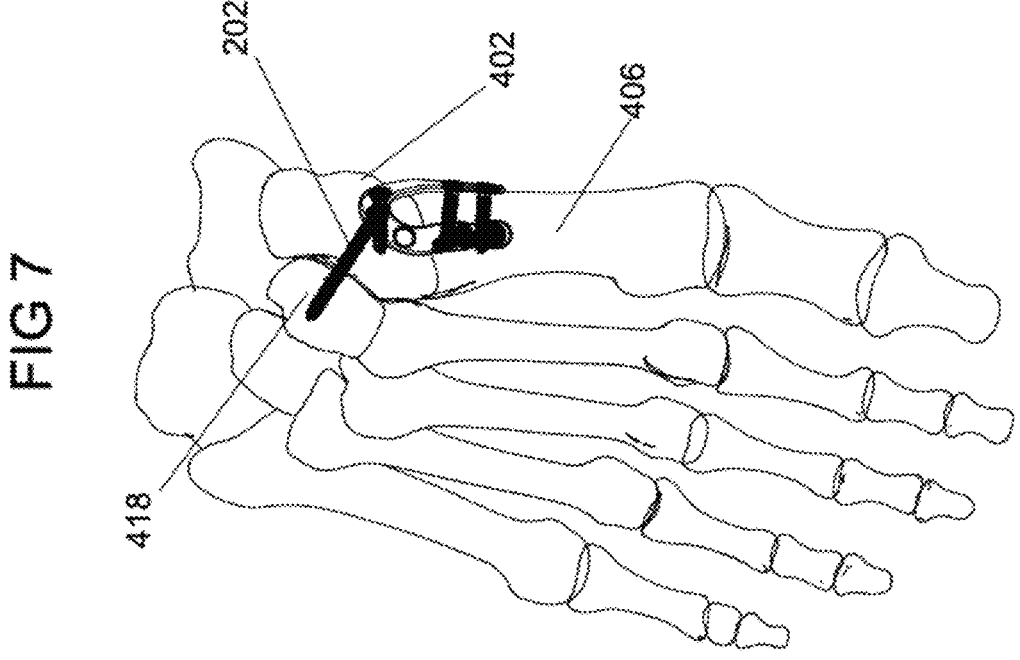
FIG. 7 is a diagram illustrating one embodiment of a fixation system on a foot.

At least in the embodiment illustrated in FIG. 7, the fixation device 202 can be inserted into the fixation hole 110 on the curved portion, into the first cuneiform 402, and/or into the second cuneiform 412. Further, various embodiments can include any suitable quantity of fixation holes 110 and use any suitable quantity of fixation devices 202 corresponding to the quantity of fixation holes 110.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device comprising:
a body comprising a curved cuneiform portion coupled to a proximal end of a dorsal extension, and a proximal end of a medial extension, and at least five fixation holes, wherein:
the fixation holes are each configured to receive a fixation device;
at least one fixation hole extends through the curved cuneiform portion, at least one fixation hole extends through the dorsal extension, and at least one fixation hole extends through the medial extension;
the curved cuneiform portion is configured to wrap around and conform to a metatarsal flare;
at least one fixation hole through the cuneiform portion is polyaxial;
the dorsal extension is configured to span a joint and the medial extension is configured to span the joint; and
a first line tangent to a distal end of the dorsal extension is approximately perpendicular to a second line tangent to a distal end of the medial extension.

2. The device of claim 1, wherein the at least one fixation hole extending through the dorsal extension and the at least one fixation hole extending through the medial extension are offset with respect to one another.

3. The device of claim 1, wherein at least one fixation hole is threaded.

4. The device of claim 1, wherein at least one fixation device is a screw.

5. The device of claim 1, wherein each fixation hole defines a respective insertion area and each fixation hole is configured to allow its respective fixation device to be inserted therein.

6. The device of claim 5, wherein at least one insertion area comprises a conical shape including an angle in the range of 25 degrees to 35 degrees.

7. The device of claim 1, wherein, the dorsal extension is configured to conform to a dorsal curvature of the first metatarsal, and the medial extension is configured to conform to a medial curvature of the first metatarsal.

8. The device of claim 7, wherein the dorsal curvature and the medial curvature are the same curvature.

9. The device of claim 1, wherein the body is configured to fixate a first metatarsal of a subject to a medial cuneiform of the subject.

10. The device of claim 1, wherein:
a distal end of the dorsal extension defines a first angle;
a distal end of the medial extension defines a second angle;
the first angle and the second angle intersect in a frontal plane at a third angle; and
the third angle is in the range of 80 degrees to 100 degrees.

11. The device of claim 10, wherein:
the curved portion comprises a dorsal portion and a medial portion;
the dorsal portion defines a fourth angle;
the medial portion defines a fifth angle;
the fourth and fifth angles intersect in the frontal plane to form a sixth angle; and
the sixth angle is in the range of 20 to 70 degrees.

12. The device of claim 1, wherein at least one fixation device is a staple.

13. A device comprising:
a body comprising a curved cuneiform portion coupled to a proximal end of a dorsal extension, and a proximal end of a medial extension, and at least five fixation holes, wherein:
at least one fixation hole extends through the curved cuneiform portion, at least one fixation hole extends through the dorsal extension, and at least one fixation hole extends through the medial extension;
each fixation hole is configured to receive a fixation device;
each fixation hole defines a respective insertion area;
the curved cuneiform portion is configured to wrap around and conform to a metatarsal flare;
at least one fixation hole through the cuneiform portion is polyaxial;
the dorsal extension is configured to span a joint and the medial extension is configured to span the joint; and
a first line tangent to a distal end of the dorsal extension is approximately perpendicular to a second line tangent to a distal end of the medial extension, the dorsal extension is configured to conform to a dorsal curvature of the first metatarsal, and the medial extension is configured to conform to a medial curvature of the first metatarsal;
a first distal end of the dorsal extension defines a first angle and a second distal end of the medial extension defines a second angle;
the first angle and the second angle intersect in a frontal plane at an angle in a range of 80 degrees to 100 degrees.

14. The device of claim 13, wherein at least one insertion area comprises a conical shape in a range of 25 degrees to 35 degrees.

15. The device of claim 13, wherein at least one fixation device is a locking screw.

16. The device of claim 13, wherein the dorsal curvature and the medial curvature are the same curvature.

* * * * *